United States Patent [19]

Colligan

[11] Patent Number: 5,722,991
[45] Date of Patent: Mar. 3, 1998

[54] APPARATUS AND METHOD FOR ATTACHING SURGICAL NEEDLE SUTURE COMPONENTS

[75] Inventor: Francis D. Colligan, New Haven, Conn.

[73] Assignee: United States Surgical Corporation, Norwalk, Conn.

[21] Appl. No.: 483,138

[22] Filed: Jun. 7, 1995

[51] Int. Cl.⁶ .................................................. A61B 17/00
[52] U.S. Cl. .................. 606/223; 606/226; 72/469; 29/515; 29/748; 29/753
[58] Field of Search .................... 606/222–227; 163/5; 289/16; 206/38; 112/222, 80.06, 80.17; 72/469, 470; 29/515–517, 748, 753

[56] References Cited

U.S. PATENT DOCUMENTS

| | | |
|---|---|---|
| Re. 27,735 | 8/1973 | Shave et al. |
| Re. 31,084 | 11/1982 | Birks . |
| 1,558,037 | 10/1925 | Morton . |
| 1,578,543 | 3/1926 | Montgomery . |
| 2,067,568 | 1/1937 | Grunthal . |
| 2,205,893 | 6/1940 | Unger . |
| 2,411,079 | 11/1946 | Baule . |
| 2,620,028 | 12/1952 | Kohut . |
| 2,958,929 | 11/1960 | Vineberg et al. |
| 2,983,898 | 5/1961 | Kalmar et al. |
| 3,055,412 | 9/1962 | Dibner . |
| 3,611,551 | 10/1971 | Shave et al. |
| 3,643,327 | 2/1972 | Jackson . |
| 3,771,343 | 11/1973 | Dawson . |
| 3,890,975 | 6/1975 | McGregor . |
| 3,910,282 | 10/1975 | Messer et al. |
| 3,963,031 | 6/1976 | Hunter . |
| 3,972,219 | 8/1976 | Riehl . |
| 3,980,177 | 9/1976 | McGregor . |
| 4,027,519 | 6/1977 | Backle . |
| 4,047,420 | 9/1977 | Edwards . |
| 4,054,144 | 10/1977 | Hoffman et al. |
| 4,060,885 | 12/1977 | Hoffman et al. |
| 4,067,224 | 1/1978 | Birks . |
| 4,072,041 | 2/1978 | Hoffman et al. |
| 4,124,027 | 11/1978 | Boss . |
| 4,192,171 | 3/1980 | Hamilton . |
| 4,292,833 | 10/1981 | Lapp . |
| 4,361,948 | 12/1982 | Omata . |
| 4,498,222 | 2/1985 | Ono et al. |

(List continued on next page.)

FOREIGN PATENT DOCUMENTS

| | | |
|---|---|---|
| 0249504 | 12/1987 | European Pat. Off. |
| 1526222 | 9/1978 | United Kingdom . |

*Primary Examiner*—Jeffrey A. Schmidt

[57] ABSTRACT

An apparatus for attaching a surgical needle of the type having an end portion with an elongated aperture defined therein and a suture having a generally elongated end portion which is to be positioned in the elongated aperture of the needle includes a pair of dies, each die having at least two generally planar engaging surfaces with a recessed portion disposed between adjacent engaging surfaces. The engaging surfaces of the dies each define a plane which is in general parallel relation to a longitudinal axis of the respective die. The recessed portion defines a relief zone such that when the end portion of the suture is positioned within the aperture of the needle end and the dies are positioned about the end portion of the needle with the engaging surfaces of each die generally facing the outer surface thereof, applying inward crimping force to the dies causes the dies to produce inward crimping forces on opposed sides of the needle end portion to cause a reduction of the dimension of the elongated aperture of the needle to thereby attach the needle to the suture whereby the recessed portion receives and collects deformed material from the needle. Secondary recessed portions may be provided to accumulate deformed needle material outward of the engaging surfaces. Side walls are provided on the die to receive the other die therebetween during crimping and constrain outward deformation of the needle. A method for attaching a surgical suture to a needle is also disclosed.

25 Claims, 6 Drawing Sheets

U.S. PATENT DOCUMENTS

| | | |
|---|---|---|
| 4,567,650 | 2/1986 | Balyasny et al. . |
| 4,672,734 | 6/1987 | Kawada . |
| 4,719,789 | 1/1988 | Wiebe et al. . |
| 4,722,384 | 2/1988 | Matsutani . |
| 4,799,311 | 1/1989 | Matsutani . |
| 4,805,292 | 2/1989 | Noguchi . |
| 4,890,614 | 1/1990 | Kawada . |
| 4,910,857 | 3/1990 | Tanaka et al. . |
| 4,922,904 | 5/1990 | Uetake et al. . |
| 5,001,323 | 3/1991 | Matsutani et al. . |
| 5,012,066 | 4/1991 | Matsutani et al. . |
| 5,046,350 | 9/1991 | Proto et al. . |
| 5,084,963 | 2/1992 | Murray . |
| 5,099,676 | 3/1992 | Proto et al. . |
| 5,131,131 | 7/1992 | Proto et al . |
| 5,168,619 | 12/1992 | Proto et al. . |
| 5,201,760 | 4/1993 | West . |
| 5,207,701 | 5/1993 | West . |
| 5,224,955 | 7/1993 | West . |
| 5,230,352 | 7/1993 | Putnam et al. . |
| 5,383,902 | 1/1995 | Carpentiere et al. .................. 606/224 |

APPARATUS AND METHOD FOR ATTACHING SURGICAL NEEDLE SUTURE COMPONENTS

BACKGROUND

1. Technical Field

The present disclosure relates to the attachment of surgical sutures to surgical needles. In particular, the disclosure relates to a method and apparatus for the attachment of surgical needles to surgical sutures to provide a combined surgical needle-suture device.

2. Background of Related Art

For many years, surgeons have employed needle-suture combinations in which a suture or ligature is attached to the shank end of a needle. Such needle-suture combinations are provided for a wide variety of monofilament and braided suture materials, both absorbable and non-absorbable, e.g., catgut, silk, nylon, polyester, polypropylene, linen, cotton, and absorbable synthetic materials such as polymers and copolymers of glycolic and lactic acids.

Needle-suture combinations fall into two general classes: standard needle attachment and removable or detachable needle attachment. In the case of standard needle attachment, the suture is securely attached to the needle and is not intended to be separable therefrom, except by cutting or severing the suture. Removable needle attachment, by contrast, is such that the needle is separable from the suture in response to a force exerted by the surgeon. Minimum acceptable forces required to separate a needle from a suture for various suture sizes are set forth in the United States Pharmacopeia (USP XXII 1990).

One typical method for securing a suture to a needle involves providing a cylindrical recess in the shank end of a needle and securing a suture therein. For example, U.S. Pat. No. 1,558,037 teaches the addition of a cement material to such a substantially cylindrical recess to secure the suture therein. Additional methods for bonding a suture within a needle bore are described in U.S. Pat. Nos. 2,928,395 (adhesives) and 3,394,704 (bonding agents). Alternatively, a suture may be secured within an axial bore in a needle by swaging the needle in the region of the recess, see, e.g., U.S. Pat. No. 1,250,114. Additional prior art methods for securing a suture within a needle bore include expansion of a catgut suture through the application of heat (U.S. Pat. No. 1,665,216), inclusion of protruding teeth within the axial bore to grasp an inserted suture (U.S. Pat. No. 1,678,361) and knotting the end of the suture to be inserted within the bore to secure the suture therein (U.S. Pat. No. 1,757,129).

Methods for detachably securing a suture to a needle are also well known. For example, U.S. Pat. Nos. 3,890,975 and 3,980,177 teach swaging a suture within a needle bore such that the suture has a pull-out value of 3 to 26 ounces. Alternative detachable attachment methods include providing a weakened suture segment (U.S. Pat. No. 3,949,756), lubricant tipping the end of a suture to be inserted in the axial bore of a needle (U.S. Pat. No. 3,963,031) and pretensioning a suture that is swaged within an axial needle bore (U.S. Pat. No. 3,875,946). See also, U.S. Pat. Nos. 3,799,169; 3,880,167; 3,924,630; 3,926,194; 3,943,933; 3,981,307; 4,124,027; and 4,127,133.

A prevailing method for forming either a detachable or non-detachable needle-suture device or combination incorporates a swage or crimp attachment. Typically, a swage or crimp attachment can be accomplished by use of a "drilled end needle", i.e., one in which a concentric aperture is formed in the end of the needle in which is the suture is placed and the needle is crimped around the suture. Examples of such attachment methods are described in the aforementioned U.S. Pat. Nos. 3,890,975 and 3,980,177. Swaging dies for achieving removable needle attachment are disclosed in U.S. Pat. Nos. 4,060,885 and 4,072,041.

The swage or crimp operations known heretofore for needle-suture attachment have their own particular shortcomings. In particular, these operations are difficult to control to achieve desired attachment parameters. Any variation in the crimping dies, the needle size, the needle aperture, or the suture size will increase variability of the needle suture attachment. Particularly with the manufacture of controlled release sutures, it heretofore has been critical to form the surgical needle to precise dimensions, i.e., the diameter of the needle and the size of the drilled hole need to be manufactured within a strict tolerance to achieve acceptable attachment. Similarly, the suture end to be attached to the needle has to be constructed within similar tight tolerances to assure that the combined tolerances of the suture and needle, when crimped with the crimping die apparatus, result in a "pull-out" force within a narrowly defined range. These manufacturing demands result in increased manufacturing time and waste and, hence, increased cost to the manufacturer.

A further disadvantage of conventional crimping operations is the distortion of the needle and lost symmetry caused by the crimping action. This is undesirable because it may result in an unacceptable pull-out force or increased trauma to tissue when the non-symmetrical needle is drawn through the tissue. For example, one conventional crimping method requires that the back end of the needle be struck with two opposed dies. The needle is then rotated 90° and the dies are arranged to strike the needle a second time. In effect, the first strike changes a round hole into one of elliptical shape, i.e., having a major and a minor axis. The second strike further distorts the needle. Furthermore, such procedures increase handling during manufacture and the likelihood that unacceptable attachment will be achieved. Indeed, rotating the suture and needle before the attachment is complete is likely to dislodge the suture tip in whole or part prior to completion of the attachment, resulting in unacceptable attachment. Moreover, multiple opposing die hits may produce a distorted needle end which results in corresponding asymmetry of tissue apertures and trauma during use.

In addition to size effects, the surface smoothness of the suture and the needle aperture, and the presence of any lubricants applied to either the suture or the needle may affect the resulting pull-out values. The conventional method of crimping, as described, underscores many of these parametric inconsistencies and necessarily utilizes multiple hits to overcome these process variabilities.

Commonly assigned U.S. Pat. Nos. 5,046,350 to Proto et al. and 5,099,676 to Proto et al. disclose crimping or swaging die configurations for attaching surgical needles and sutures. The split ring die disclosed in U.S. Pat. No. 5,046,350 includes a relief zone defined between a pair of extensions. A needle positioned between a pair of the split ring dies is stricken by the extensions whereby the superfluous material caused by the swaging action collects within the relief zone. The novel configuration of the split ring die provides a more uniform swage while the needle retains its circular symmetry in the area of suture attachment.

U.S. Pat. No. 5,099,676 discloses a die featuring a novel clover leaf shape which is defined by a generally circular surface having a series of interconnected alternating individual convex and concave curved surfaces. The convex and concave surfaces permit needle material swaged during the crimping process to flow from the convex portions which perform the actual crimping action to the concave areas so as to collect within the concave portions. The clover leaf dies provide unique attachment of the suture components and also maintains the symmetry of the product.

Although the crimping dies disclosed in the Proto et al. '350 and '676 patents have proven to be extremely effective for their intended purposes, the present disclosure is directed to further improvements whereby surgical needles and sutures of various sizes and types may be attached to desired attachment parameters. In accordance with the method and apparatus of the present disclosure, attachment is achieved while retaining the symmetry of the needle. Only a single "hit" on the needle end is required to accomplish the attachment thus minimizing handling of the suture and needle and reducing process control requirements.

SUMMARY

Generally stated, the present disclosure is directed to an apparatus for attaching a surgical needle having an end portion with an elongated aperture defined therein and a suture having a generally elongated end portion which is to be positioned in the elongated aperture of the needle. The apparatus includes a pair of dies, each die having at least two generally planar engaging surfaces with a recessed portion disposed between adjacent engaging surfaces. The engaging surfaces of the dies each define a plane which is in general parallel relation to a longitudinal axis of the respective die. The recessed portion defines a relief zone such that when the end portion of the suture is positioned within the aperture of the needle end and the dies are positioned about the end portion of the needle with the engaging surfaces of each die generally facing the outer surface thereof, applying inward crimping force to the dies causes the dies to produce inward crimping forces on opposed sides of the needle end portion to cause a reduction of the dimension of the elongated aperture of the needle to thereby attach the needle to the suture whereby the recessed portion receives and collects deformed material from the needle.

In a preferred embodiment, each die includes two generally planar engaging surfaces which extend transversely relative to a longitudinal bisecting plane defined by the die and one recessed portion disposed therebetween. The recessed portion extends along the longitudinal axis of the respective die and is generally arcuately shaped. Preferably, the recessed portion extends the lengths of the engaging surfaces. The engaging surfaces uniquely apply a concentrated force to the needle end to cause localized deformation thereof thereby ensuring the desired suture attachment.

The die configuration advantageously permits a wide range of sutures of different sizes to be attached to a single diameter bore in the needle without causing any cracking or failure at the needle-suture attachment and can be utilized to form detachable needle-suture combinations (i.e., where the suture may be readily separated from the needle by a predetermined force by the user) or non-detachable needle-suture combinations (where separation of the suture is accomplished by cutting or the like).

The present disclosure is also directed to a method for attaching a surgical needle having an end with an elongated aperture formed therein to a suture. The method includes the steps of providing a pair of dies with each die having a die surface portion with two generally planar engaging surfaces and a recessed portion disposed between the two engaging surfaces, positioning the pair of dies adjacent the needle end with the two engaging surfaces facing the outer surface of the needle end in general parallel relation with a longitudinal axis defined by the elongated aperture of the needle end and the recessed portion extending along the direction of the needle end which defines the elongated aperture and applying inward impact force to the dies to displace the dies toward each other causing the two engaging surfaces of each die to engage the outer surface of the needle end to thereby cause crimping of the needle end and reduction of an average dimension of the aperture defined therein, whereby the recessed portion disposed between the engaging surfaces is configured and dimensioned to permit deformed material of the needle to be received and collected therewithin so as to facilitate attachment of the needle and the suture.

A needle-suture combination formed by the apparatus and method of the present disclosure is also disclosed.

BRIEF DESCRIPTION OF THE DRAWINGS

Various embodiment(s) of the present disclosure is/are described herein with reference to the drawings, wherein.

DETAILED DESCRIPTION OF THE PREFERRED EMBODIMENTS

Figure 1:
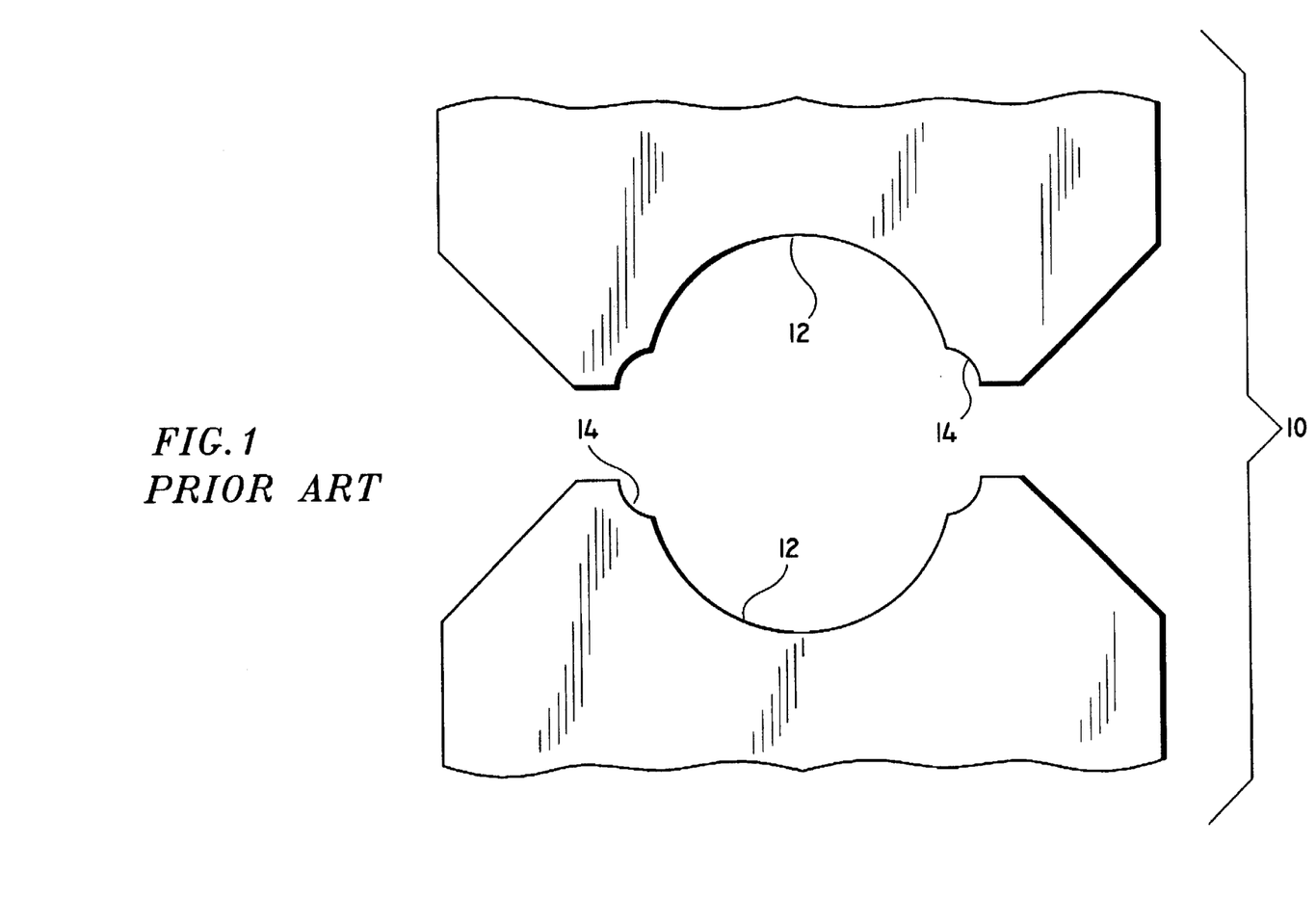
FIG. 1 is an axial plan view of a pair of conventional dual lap-overlap semicircular shaped dies.

Referring initially to FIG. 1, there is illustrated a pair of prior art dies 10 of a type utilized to attach a suture to a surgical needle. Each die 10 has a working surface at 12 of generally semi-circular shape and adjacent arcuate corner portions 14 to receive limited amounts of excess needle material overflowing during the crimping or swaging process. As shown, the arcuate corner portions 14 are of lesser radii than the working surface 12 and are not concentric therewith.

To attach a needle to a suture, the dies 10 are positioned within an apparatus as will be described hereinbelow. The apparatus is arranged to cause both dies 10 to simultaneously move toward each other and strike a needle positioned between them. This causes the needle to become elliptical in cross-section and causes portions of the needle to deform into corner portions 14. Once the dies are impacted toward each other, they are separated and the needle is rotated 90°. The dies are then struck once again and the attachment is completed. In essence, the first strike causes the circular aperture in the needle to become elliptical. The second strike completes the attachment and reverses the distortion imparted to the needle. In certain instances, additional hits are required to positively secure the suture to the needle. This procedure necessitates at least a dual step attachment which in turn requires additional time and labor and results in loss symmetry of the needle end as stated above.

Figure 2:
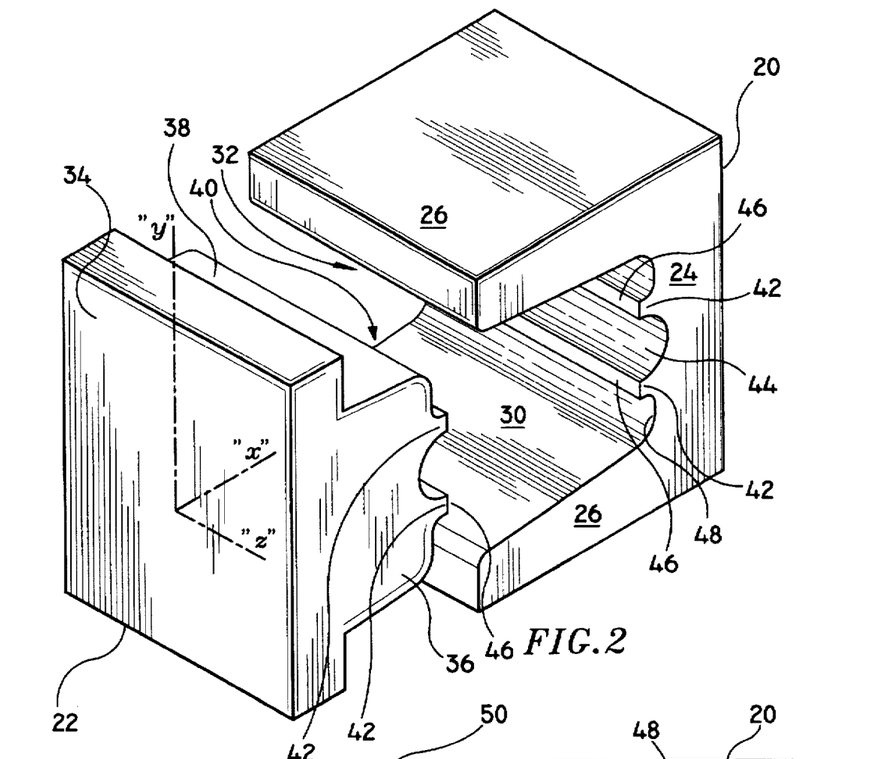
FIG. 2 is a perspective view of the swaging dies constructed in accordance with the principles of the present disclosure.
Figure 3:
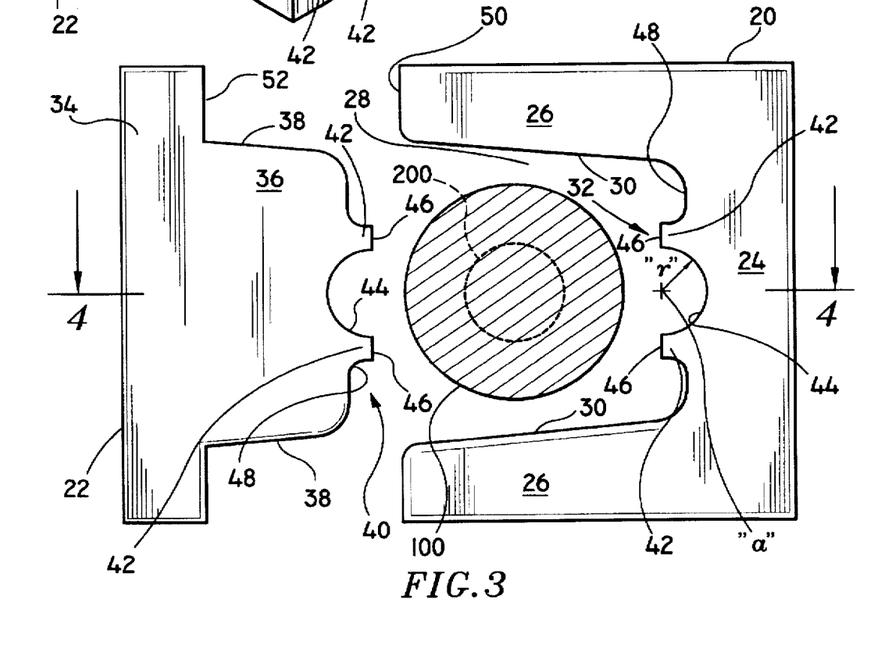
FIG. 3 is an axial plan view of the dies of FIG. 2 in an initial open position illustrating a needle end positioned between the dies.
Figure 4:
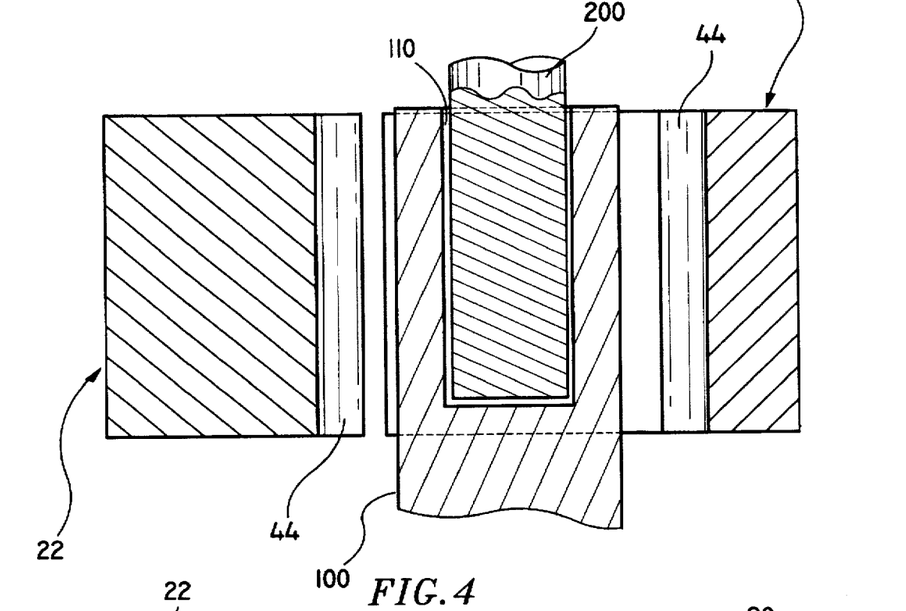
FIG. 4 is a cross-sectional view of the dies taken along the lines 4—4 of FIG. 3.

Referring now to FIGS. 2–4, there is illustrated a pair of dies constructed according to the principles of the present disclosure. Dies 20, 22 are contemplated for use in attaching a needle of the type having a blunt end with a generally elongated aperture formed therein (i.e., a drilled needle) and a suture defining an end portion which is positioned within the elongated aperture of the needle. Dies 20, 22 are advantageously configured to attach surgical sutures and needles of various sizes and types.

The particular arrangement of the dies 20, 22 is best depicted in the axial view of FIG. 3 in which the dies 20, 22 are shown with the blunt end portion of surgical needle 100 therebetween in a position to be attached to a suture 200 (shown in phantom) and in the cross-sectional view of FIG. 4 taken along lines 4—4 of FIG. 3. In FIGS. 2–4, the dies 20, 22 are shown separated from each other in position prior to impact on a surgical needle 100. Surgical needle 100 has an aperture 110 where the end portion of suture 200 is positioned as best depicted in FIG. 4.

Die 20 includes base 24, and a pair of die side walls 26 extending outwardly from the base 24. Die side walls 26 define an inner cavity 28 therebetween which accommodates the drilled end portion (i.e., having aperture 110) of needle 100 during the swaging process. The inner surfaces 30 of die walls 26 taper outwardly toward the open end of die 20 to facilitate the relative inward swaging movement of dies 20, 22 as will be discussed hereinbelow. Die 20 also includes inner die surface 32.

Die 22 includes base 34 and die extension 36 projecting outwardly from the base 34. Die extension 36 is correspondingly dimensioned and configured to be received within inner cavity 28 of die 20 during the needle swaging process and defines outer surfaces 38 which taper inwardly at a similar angle of inclination as that of inner surfaces 30 of die 20. Die 22 also includes an inner die surface 40.

Each die 20, 22 defines an x-axis, a y-axis and a z-axis as shown in FIG. 2.

Referring still to FIGS. 2–4, inner die surfaces 32, 40 of dies 20, 22, respectively, are substantially identical with each surface including first and second raised swaging portions 42 separated by a concavity or recessed portion 44 as shown. Swaging portions 42 have substantially planar swaging surfaces 46 which contact the drilled needle end during the swaging process. Swaging surfaces 46 extend along the longitudinal axis, i.e., the z-axis (FIG. 2) of the dies 20, 22. In the preferred embodiment swaging surfaces 46 extend generally transversely relative to a longitudinal bisecting plane, i.e., the "xz" plane shown in FIG. 2 of the dies 20, 22 and in general parallel relation to a vertical plane, i.e., the "yz" plane also shown in FIG. 2.

Each concavity 44 is generally arcuately-shaped and preferably defines a radius "r" (FIG. 3) which remains constant throughout its length. Each concavity 44 extends along the entire longitudinal length of inner die surfaces 32, 40 as best shown in FIGS. 2 and 4 and defines a material relief zone to receive needle material displaced by the dies 20, 22 when the dies are caused to strike the drilled needle end during swaging. As depicted in FIG. 3, the axis "a" of each concavity 44 extends in generally parallel relation to a longitudinal axis, i.e., the z-axis, of the dies 20, 22.

Inner die surfaces 32, 40 of dies 20, 22 further include secondary recessed portions 48 which are disposed adjacent the outer areas of swaging portions 42. Secondary recessed portions 48 define a generally arcuate shape and may serve as material relief zones (FIGS. 2 and 3) to accommodate needle material overflow which accumulates during swaging of the needle end, particularly if a relatively large diameter needle is swaged.

Figure 5:
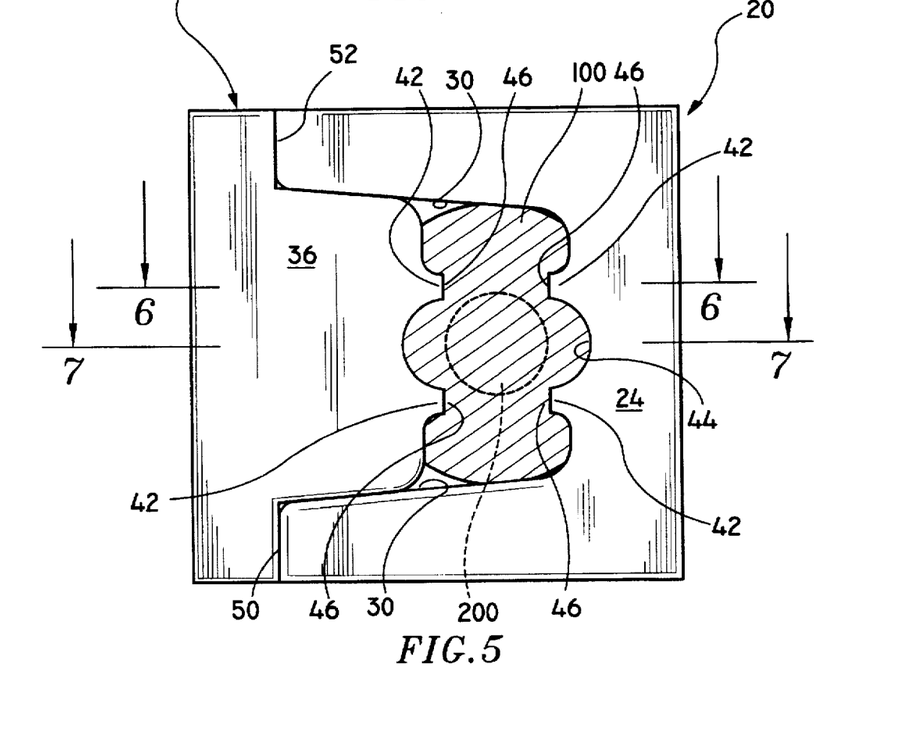
FIG. 5 is an axial plan view of the dies in an approximated closed position swaging the needle end.
Figure 6:
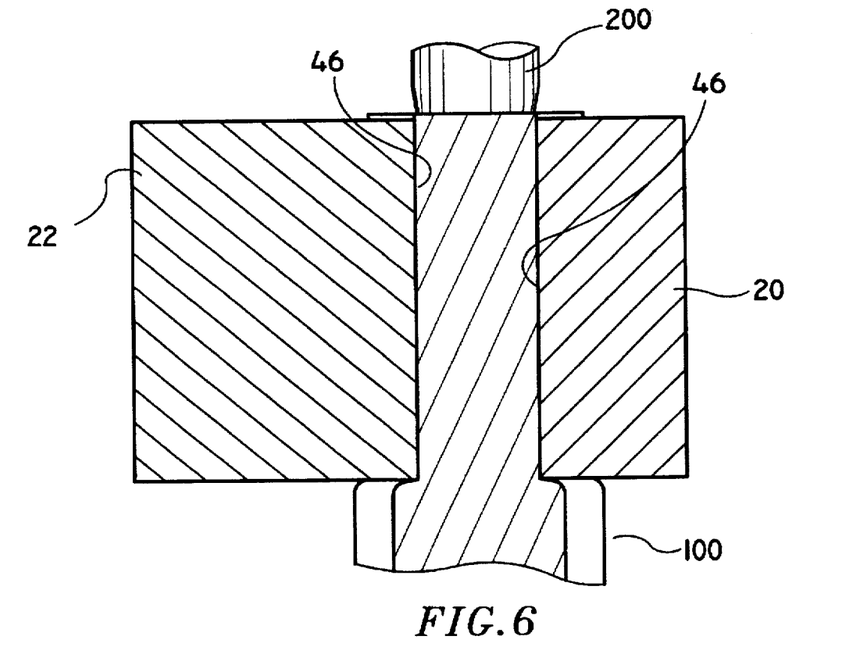
FIG. 6 is a cross-sectional view of the dies taken along the lines 6—6 of FIG. 5 illustrating the relative depth of the swage produced on the needle end.
Figure 7:
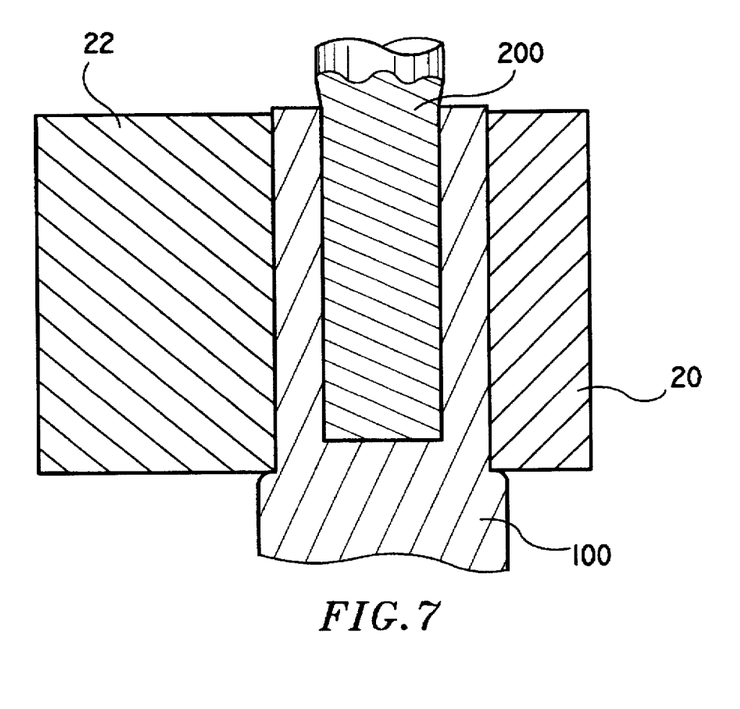
FIG. 7 is a cross-sectional view of the dies taken along the lines 7—7 of FIG. 5 illustrating the relief zones of the dies for accumulating needle material overflow displaced during the swaging.

FIGS. 5–7 illustrate the swaging effect dies 20, 22 produce on the drilled needle end. During the swaging process, dies 20, 22 are moved toward each other until dies faces 50, 52 of dies 20, 22, respectively (FIG. 3), meet whereby planar swaging surfaces 46 strike the drilled end portion of needle 100. The correspondingly dimensioned surfaces 30, 38 of dies 20, 22 insure proper alignment of the dies 20, 22 during the inward swaging movement.

FIG. 5 is a view similar to the view of FIG. 3, but depicts the dies in an approximated position swaging the needle end. As shown in FIG. 5, with die surfaces 50, 52 contacting one another, the swaging surfaces 46 on each of dies 20, 22 are approximated to a predetermined position to appropriately compress or swage the drilled needle end or needle attachment portion of the needle 100 to secure the suture 200 within needle aperture 110. As shown, inner surfaces 30 of die 20 limit and control the outward expansion of the needle 100 in response to the compressive forces exerted on the needle by swaging surfaces 32, 40. Preferably, the end of the needle 100 is not permitted to expand outwardly significantly greater then the original diameter of the needle 100 prior to swaging, and is constrained so as to prevent formation of sharp edges or "fins".

FIGS. 6 and 7 are cross-sectional views taken along lines 6—6 and 7—7, respectively, of FIG. 5 illustrating the swaging effects on the needle. FIG. 6 illustrates in cross-section, the amount of radial inward movement of each die 20, 22 and the swaging action of planar swaging surfaces 46 on the drilled needle end. The needle material which is engaged and displaced by planar swaging surfaces 46 accumulates by the swaging action into the relief zones defined by concavities 44 of the dies. FIG. 7 illustrates in cross-section, the needle material displacement into concavities 44. It is also envisioned that some of the needle material displaced may flow into secondary recessed portions 48, as shown in FIG. 5. As stated above, this will occur when a relatively large diameter needle is being swaged. Simultaneously, with the swaging action, the needle portion defining the aperture 110 of the needle 100 will be effectively crimped and attached to suture 200 by the physical reduction of the dimension of the aperture 110 surrounding the suture.

Advantageously, the dies of the present disclosure require only one strike or "hit" to effect attachment of the suture components, thus, eliminating the double-hit method along with its inherent disadvantages. Preferably, dies 20, 22 produce a non-detachable needle-suture combination, i.e., a "permanently" attached needle suture, however, it is contemplated that detachable needle-suture combinations also may be made with the dies 20, 22. A further significant advantage of the present dies 20, 22 resides in the fact that they advantageously allow sutures of a wide diameter range to be used with a single diameter bore hole in the needle without causing any cracking or other failure of the needle at the drilled needle end due to the swaging. This appears to be attributed to the 1) unique capturing of the needle entirely within the dies 20, 22 during swaging; 2) the concentrated force of the dies 20, 22, i.e., die surfaces 46, upon inward deformation of the needle end; and 3) the sufficient depth of the crimp as provided by swaging portions 42.

Figure 8:
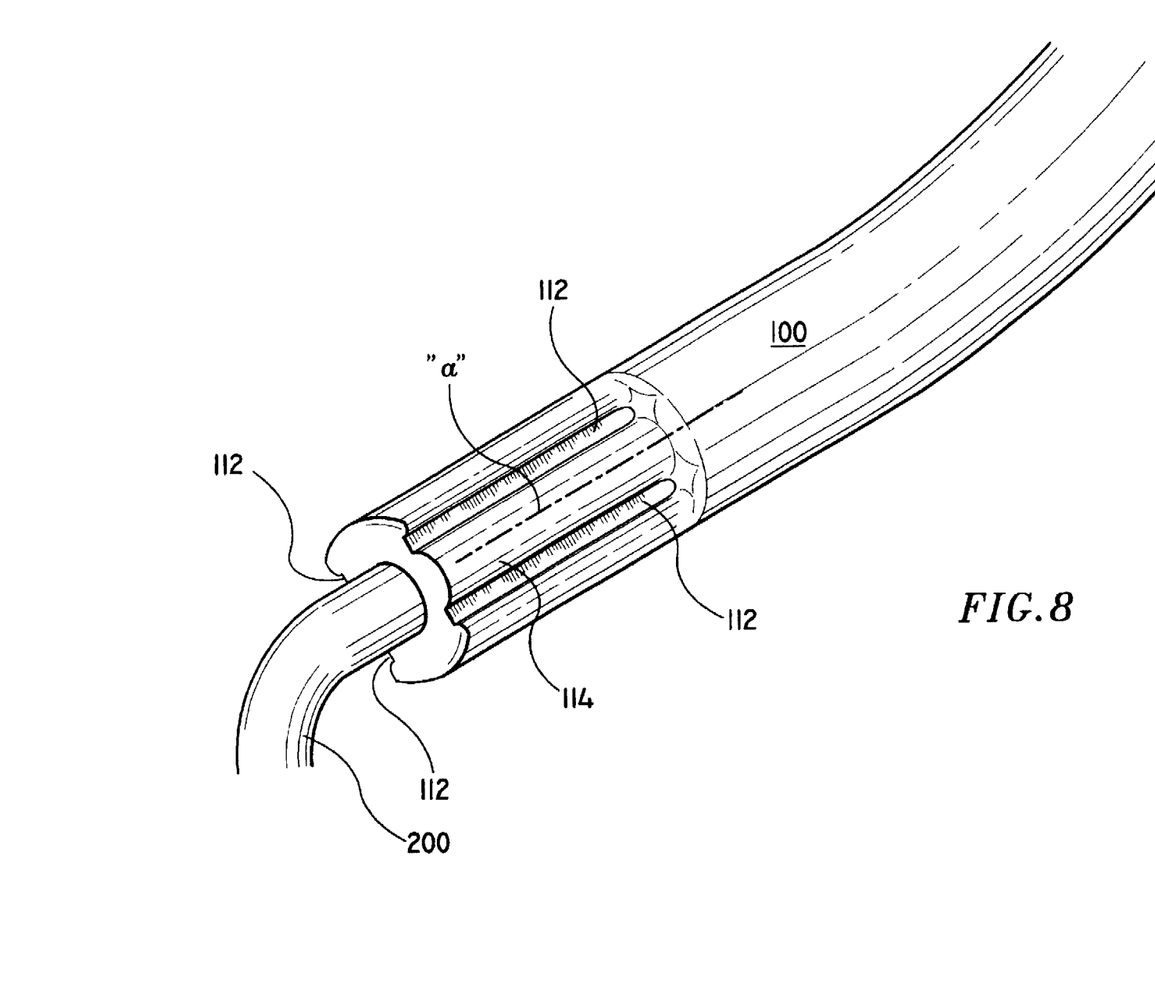
FIG. 8 is a perspective view of the needle end with attached suture as provided with the dies of the present disclosure.

Referring now to FIG. 8, the configuration of the needle 100 subsequent to attachment by dies 20, 22 to suture 200 is illustrated. The planar swaging surfaces 46 of the dies 20, 22 produce generally planar surface portions 112 on the drilled end of the needle 100. The planar surface portions 112 extend generally longitudinally relative to the longitudinal axis "a" of the needle 100. The centrally disposed arcuate raised portion 114 present on the needle end reflects the relief zone defined by recessed portion 44 of the dies 20, 22 where the material overflow is received during swaging. Secondary raised arcuate portions 116 disposed outwardly of planar surface portions 112 reflect accumulation of needle material in secondary relief zones defined by secondary recessed portions 48 and constraint upon the needle by side walls 30. As shown, needle-suture attachment is achieved while maintaining the general symmetry of the needle with relatively insignificant surface distortion except for the minor impressions formed on the surface by the engaging surfaces. Thus, the needle 100 retains its generally circular symmetry in the area of suture attachment which thereby minimizes tissue trauma during the suturing process.

Figure 9:
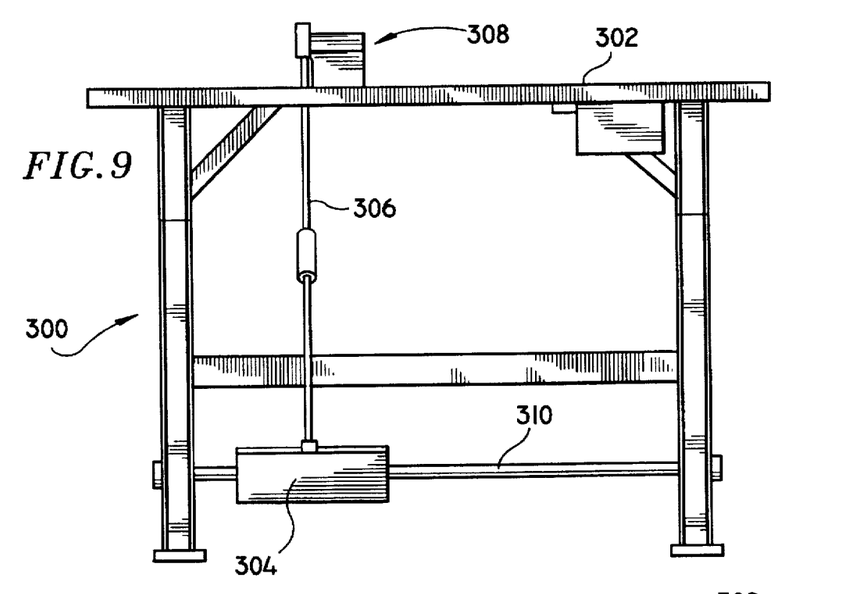
FIG. 9 is a front view of an apparatus with which the dies constructed according to the present disclosure may be utilized to attach a suture to a needle by crimping.
Figures 10, 11, 12:
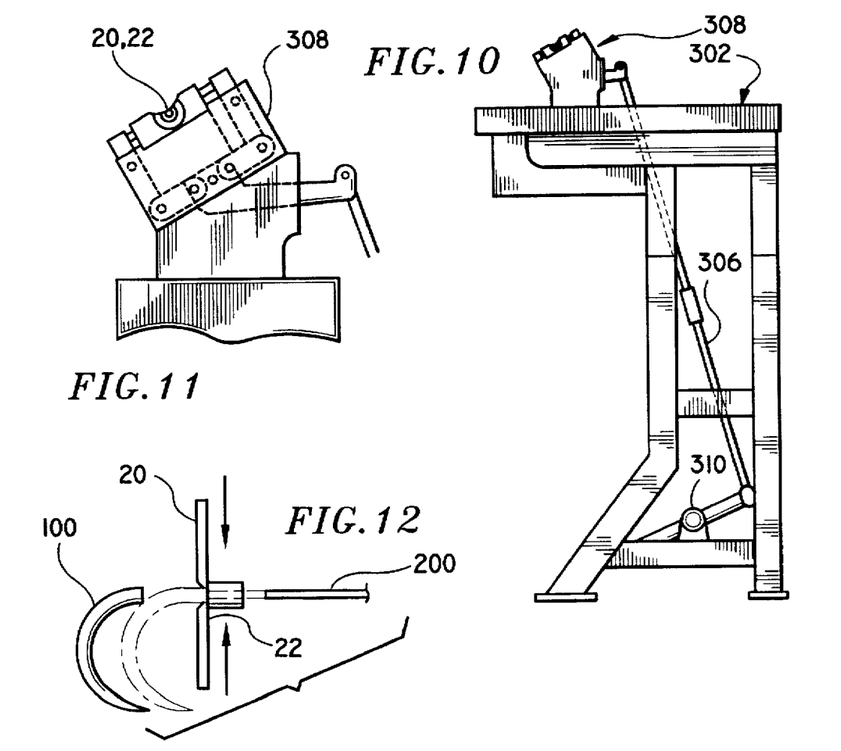
FIG. 10 is a side view of the apparatus shown in FIG. 9.
FIG. 11 is an enlarged view illustrating the dies of the present disclosure mounted in the apparatus of FIG. 9 for attaching a suture to a needle.
FIG. 12 is an enlarged side view of a pair of dies constructed according to the present disclosure positioned to attach a suture to a curved surgical needle.

Referring now to FIGS. 9 and 10 there is shown an exemplary apparatus 300 on which sutures may be attached to needles utilizing the pair of dies 20, 22 of the present disclosure. The apparatus 300 shown is manufactured and marketed as model 6A Suture Attaching Machine by B. G. Sulzel, Inc., Syracuse, N.Y. Other comparable machines suitable for attaching sutures may be utilized with the dies of the present disclosure.

The suture attaching machine 300 as illustrated in FIG. 9 includes a table 302 having treadle 304 which is foot operated and connected via treadle rod 306 to suture press 308. The treadle 304 is mounted for pivotal movement on pivot rod 310.

Referring now to FIG. 11, there is shown an enlarged side view of the suture press 308. As can be seen in FIG. 11, the pair of dies 20, 22 which are constructed according to the disclosure are positioned within the jaws of the suture press 308 and arranged to be stricken against a needle 100 with the suture 200 in position as shown in FIG. 12.

The needle 100 shown in FIG. 12 is of a curved type having a straight rear end portion which defines an elongated aperture 110 dimensioned for reception and attachment to an appropriately sized suture 200. The needle 100 is supported on a guide support having a "V shaped" guide channel which positively determines and positions the needle location and orientation as shown. Thereafter, appropriate adjustments are made to predetermine the strike force to be transmitted to the needle and suture as may be appropriately calculated to obtain a predetermined pull-out force. The treadle is depressed to cause the dies to strike the needle.

An alternative apparatus for attaching surgical sutures to needles is disclosed in commonly assigned U.S. Pat. No. 5,350,373, which issued on Sep. 27, 1994, the contents of which are incorporated herein by reference. This apparatus includes a frame for positioning and maintaining the needle while the suture is being attached and a die system which selectively impacts the needle to secure the needle thereto. The die system may be modified to incorporate the novel dies 20, 22 of the present disclosure.

It will be readily appreciated that the dies 20, 22 of the present disclosure are particularly advantageous in that many types of sutures may be readily attached to needles having an aperture in their blunt end, i.e., drilled end needles. Further, single strike force is utilized thereby avoiding the need to provide "double-hit" attachment as necessary with prior art dies. This procedure provides a surgical needle-suture combination having a needle which is substantially symmetrical. Moreover, the single-hit attachment procedure provides consistent and controlled attachment of the suture and the needle which additionally reduces the time and effort to complete the attachment. Die life is increased, rejected needle/suture attachments are reduced, and attachment time is reduced. As a result, the cost of producing a surgical suture may be reduced.

The swaging dies 20, 22 of the present disclosure may be utilized with all types of needles such as curved needles, straight needles, or the like, provided they have an elongated aperture on their end portion for receiving the suture. The elongated aperture preferably is a drilled hole, but also could be a channel formed in the end of the needle. Sutures usable with the present disclosure include silk, nylon, linen, cotton, polyester, polypropylene, stainless steel, natural materials such as catgut, synthetic polymers having glycolic acid ester linkages subject to hydrolytic degradation to non-toxic tissue compatible absorbable components, including polyglycolic acid. The sutures may be monofilamentary or braided, absorbable or non-absorbable. The dies of the present disclosure are preferably constructed of a hardened material such as tungsten carbide. However, it should be understood that all materials suitable for such die construction may be used, provided the geometric and configurational parameters taught by the present disclosure are met.

While the above description contains many specifics, these specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. A surgical needle-suture attachment apparatus for attaching a surgical needle and a suture, which comprises a pair of dies, and a surgical needle at least partially positioned within the dies and having an end portion with an elongated aperture defined therein, each die including at least two generally planar engaging surfaces with a recessed portion disposed between adjacent engaging surfaces, the engaging surfaces each defining a plane in general parallel relation to a longitudinal axis of the respective die, the recessed portion defining a relief zone such that when an end portion of the suture is positioned within the aperture of the needle end and the dies are positioned about the end portion of the needle with the at least two engaging surfaces of each die generally facing the outer surface of the needle, applying inward crimping force to the dies causes the dies to produce inward crimping forces on opposed sides of the needle end portion to cause a reduction of the dimension of the elongated aperture of the needle to thereby attach the needle to the suture, wherein the recessed portion between the adjacent planar engaging surfaces is configured for receiving and collecting deformed material from the needle.

2. The apparatus according to claim 1 wherein each die includes two generally planar engaging surfaces with one recessed portion disposed between the two generally planar engaging surfaces.

3. The apparatus according to claim 2 wherein the recessed portion extends along the longitudinal axis of the respective die.

4. The apparatus according to claim 3 wherein the recessed portion of each die is generally arcuate.

5. The apparatus according to claim 4 wherein the recessed portion has a generally semicircular shape in cross-section defining a radius of curvature which is substantially constant throughout its length.

6. The apparatus according to claim 3 wherein the two planar engaging surfaces of each die extend in a longitudinal direction with respect to the longitudinal axis of the respective die.

7. The apparatus according to claim 6 wherein the recessed portions extend the lengths of the dies.

8. The apparatus according to claim 6 wherein the two planar engaging surfaces of each die define planar portions which are generally transverse to a longitudinal bisecting plane defined by the die.

9. The apparatus according to claim 8 wherein the planar portions defined by the two planar engaging surfaces of each die lie in the same plane.

10. The apparatus according to claim 1 wherein one of the dies has side die walls configured to surround the end portion of the needle, at least a portion of the other of the dies being insertable between the side die walls during swaging.

11. The apparatus according to claim 1 wherein each die further comprises at least one secondary recessed portion not between the engaging surfaces.

12. The apparatus according to claims 10 wherein the die having side walls includes at least one secondary recessed portion.

13. The apparatus according to claim 12 wherein the die having side walls includes a pair of secondary recessed portions.

14. A method for attaching a surgical needle to a suture, the needle having an end with an elongated aperture formed therein, the suture having an end portion suitably configured for insertion into the aperture, the method comprising the steps:

provid­ing a pair of dies, each die including a die surface portion having at least two generally planar engaging surfaces and a recessed portion disposed between the two engaging surfaces;

positioning the pair of dies adjacent the needle end with the two engaging surfaces facing the outer surface of the needle end in general parallel relation with a longitudinal axis defined by the elongated aperture of the needle end and the recessed portion extending along the direction of the needle end which defines the elongated aperture; and applying inward impact force to the dies to displace the dies toward each other causing the two engaging surfaces of each die to engage the outer surface of the needle end to thereby cause crimping of the needle end and reduction of an average dimension of the aperture defined therein, whereby the recessed portion disposed between the engaging surfaces is configured and dimensioned to permit deformed material of the needle to be received and collected therewithin so as to facilitate attachment of the needle and the suture.

15. The method according to claim 14 wherein the step of providing includes providing a die having planar portions, the planar portions being defined by the two engaging surfaces, the planar portions being generally transverse relative to a longitudinal bisecting plane of the die.

16. The method according to claim 15 wherein the step of providing includes providing the dies with recessed portions extending the entire length of the engaging surfaces.

17. The method according to claim 15 wherein the step of providing includes providing a die having a recessed portion with an arcuate cross-section defining a radius of curvature which is constant throughout its length.

18. The method according to claim 14 wherein the step of providing includes providing at least one of the dies having opposed side walls, the other die being received between the side walls when applying inward impact force to the dies and the side walls constraining the needle during crimping.

19. The method according to claim 18 wherein the step of providing includes providing the at least one die having a pair of secondary recessed portions, each secondary recessed portion being disposed between a side wall and an engaging surface and dimensioned for receiving and collecting deformed material of the needle.

20. The method according to claim 14 wherein the step of applying includes applying impact force to the dies such that the suture is permanently attached to the needle.

21. A needle-suture combination, which comprises:

a) a surgical needle including a sharp end and a blunt end, the blunt end defining an elongated aperture therein;

b) a suture having a generally elongated end portion which is positioned within the elongated aperture of the needle; and c) a portion of the blunt end swaged to cause attachment of the needle to the suture, the swaged portion including at least two generally coplanar surface portions in general parallel relation to a longitudinal axis defined by the elongated aperture of the needle and at least one substantially arcuate raised portion disposed between adjacent coplanar surface portions and contiguous therewith.

22. The needle-suture combination according to claim 21 wherein the swaged portion of the needle includes first and second pairs of opposed generally coplanar surface portions, each pair of coplanar surface portions having a substantially arcuate raised portion therebetween.

23. The needle-suture combination according to claim 22 wherein the two planar surface portions of the first pair of coplanar surface portions lie substantially in a first plane and wherein the two coplanar surface portions of the second pair lie substantially in a second plane and wherein the first and second planes are in general parallel relation with each other.

24. The needle-suture combination according to claim 21 wherein the swaged portion of the needle is configured and dimensioned to engage the suture such that the suture is non-detachably attached to the needle.

25. The needle-suture combination according to claim 21 wherein the swaged portion of the needle further includes secondary raised arcuate portions disposed outwardly of the generally coplanar surface portions.

* * * * *